(12) United States Patent
Chan et al.

(10) Patent No.: US 6,624,510 B1
(45) Date of Patent: Sep. 23, 2003

(54) ELECTRODE ARRAY HAVING A THIN, FLEXIBLE SUBSTRATE

(75) Inventors: Winston K. Chan, Princeton, NJ (US); Chris Coretsopoulos, Iowa City, IA (US); Matthew A. Howard, III, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/672,443

(22) Filed: Sep. 28, 2000

(51) Int. Cl.[7] .............................................. H01L 23/52
(52) U.S. Cl. ...................................... 257/734; 600/377
(58) Field of Search ................................ 257/734, 739; 600/377

(56) References Cited

U.S. PATENT DOCUMENTS

| | | |
|---|---|---|
| 4,735,208 A | 4/1988 | Wyler et al. |
| 4,763,660 A * | 8/1988 | Kroll et al. .................... 439/77 |
| 4,819,648 A | 4/1989 | Ko |
| 4,869,255 A | 9/1989 | Putz |
| 4,903,702 A | 2/1990 | Putz |
| 5,097,835 A | 3/1992 | Putz |
| 5,215,088 A | 6/1993 | Normann et al. |
| 5,496,369 A | 3/1996 | Howard, III |
| 5,676,655 A | 10/1997 | Howard, III et al. |
| 5,697,975 A | 12/1997 | Howard, III et al. |
| 5,698,083 A * | 12/1997 | Glass .................... 207/403.03 |
| 5,713,847 A | 2/1998 | Howard, III et al. |
| 5,735,885 A | 4/1998 | Howard, III et al. |
| 5,776,111 A * | 7/1998 | Tesio .......................... 604/174 |
| 5,800,535 A | 9/1998 | Howard, III |
| 5,820,588 A | 10/1998 | Howard, III |
| 5,843,093 A | 12/1998 | Howard, III |
| 5,902,236 A | 5/1999 | Iversen |
| 5,938,689 A | 8/1999 | Fischell et al. |
| 6,024,702 A | 2/2000 | Iversen |
| 6,052,608 A | 4/2000 | Young et al. |
| 6,201,707 B1 * | 3/2001 | Sota .......................... 174/260 |

* cited by examiner

*Primary Examiner*—Nathan J. Flynn
*Assistant Examiner*—Leonardo Andújar
(74) *Attorney, Agent, or Firm*—Fleshner & Kim, LLP

(57) ABSTRACT

An electrode array includes a flexible substrate, and a plurality of electrodes disposed on the flexible substrate. The flexible substrate is preferably formed of polyimide. The contacts preferably have a diameter in the range of approximately 10 $\mu$m to 1 mm. The an electrode array is manufactured by forming a plurality of electrodes on a flexible substrate by forming a metal line on the flexible substrate for each of the plurality of electrodes by depositing one or more metals using electron beam evaporation and then patterning the one or more metals and forming a contact on the flexible substrate for each of the plurality of electrodes using one of electroplating and embossing, and then forming an insulating film on the flexible substrate except over the contacts and areas of the electrodes utilized for connections to an electrical device. Electroplating is utilized to form contacts less than approximately 100 $\mu$m in diameter, and embossing is utilized to form contacts greater than approximately 100 $\mu$m in diameter.

29 Claims, 1 Drawing Sheet

ELECTRODE ARRAY HAVING A THIN, FLEXIBLE SUBSTRATE

BACKGROUND OF THE INVENTION

1. Field of the Invention

This invention relates to an electrode array and a method of manufacturing an electrode array, and in particular, to a neurological electrode array microfabricated on a flexible substrate utilizing biocompatible materials.

2. Background of the Related Art

A current challenge in the neural sciences is to monitor and to simulate neural activity with high spatial resolution. This requires a large number of electrodes within a small area, and independent, low noise connections to data acquisition equipment. Current microfabrication techniques are capable of making these electrode arrays, but the potential use on human subjects greatly restricts the materials and physical characteristics that can be employed.

SUMMARY OF THE INVENTION

An object of the invention is to solve at least the above problems and/or disadvantages and to provide at least the advantages described hereinafter.

A further object of the invention is to provide a small biocompatible electrode array that can be utilized for electrophysiologic studies in humans and other mammals.

Another object of the invention is to create significantly high contact density than currently commercially available devices.

An electrode array according to a preferred embodiment of the invention includes a flexible substrate, and a plurality of electrodes disposed on the flexible substrate. The flexible substrate is preferably formed of polyimide. The contacts preferably have a diameter in the range of approximately 10 $\mu$m to 1 mm, more preferably approximately 30 $\mu$m to 200 $\mu$m.

The electrode array is manufactured according to a preferred method of the invention by forming a plurality of electrodes on a flexible substrate by forming a metal line on the flexible substrate for each of the plurality of electrodes by depositing one or more metals using electron beam evaporation and then patterning the one or more metals. A contact is then formed on the flexible substrate for each of the plurality of electrodes using one of electroplating and embossing. An insulating film is formed on the flexible substrate except over the contacts and areas of the electrodes utilized for connections to an electrical device. Preferably, electroplating is utilized to form contacts less than approximately 100 $\mu$m in diameter, and embossing is utilized to form contacts greater than approximately 100 $\mu$m in diameter.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

With human subjects, it is imperative that surface electrodes do not penetrate brain tissue. An array of surface electrodes must be provided on a flexible, conformable substrate if all of the electrodes are to contact the curved surface of the brain simultaneously without penetration.

Figures 1A, 1B:
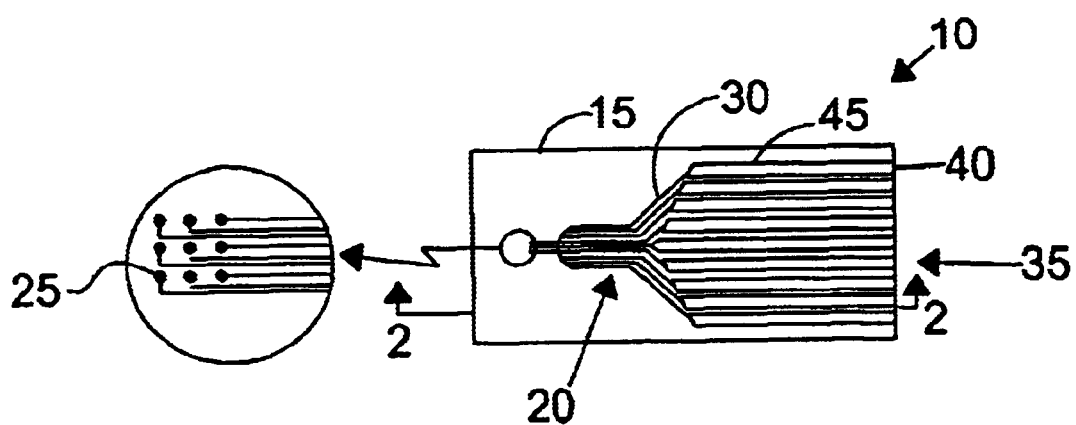
FIG. 1A is a schematic top view drawing of an electrode array according to a preferred embodiment of the invention.
FIG. 1B is a magnified view of a portion of the electrode array showing electrode contacts.
Figure 2:
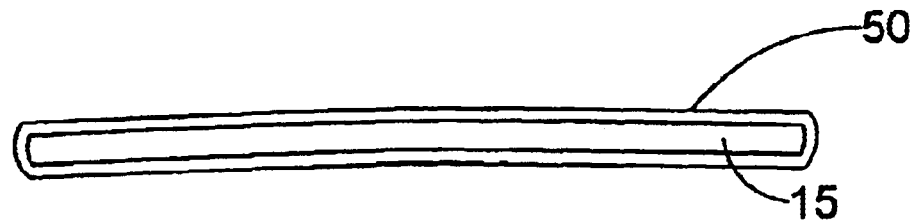
FIG. 2 is a side view of the electrode array according to a preferred embodiment of the invention taken along line 2—2 of FIG. 1A.

FIG. 1B is a schematic drawing of a neurological electrode array according to the invention. The neurological electrode array 10 includes a flexible substrate 15. The flexible substrate 15 is preferably a thin flexible substrate, and more preferably a thin flexible substrate between approximately 0.01" and 0.01" in thickness, and even more preferably a polyimide substrate, and even more preferably a commercially available 0.003" (76 $\mu$m) thick polyimide substrate. The flexible substrate should tolerate the chemicals and the temperature cycling required to microfabricate the electrodes. Polyimide is an example of a material that does provide such toleration during the microfabrication process.

An array of electrodes 20 is microfabricated on a surface of the flexible substrate 15. Each electrode in the array includes a contact 25. The contact 25 makes contact with the brain. The contact 25 is preferably formed of platinum; however, other materials may also be appropriate. The contacts 25 preferably range from approximately 10 $\mu$m to 1 mm in diameter, more preferably approximately 30 $\mu$m to 200 $\mu$m.

Each electrode further includes an area 40 at an edge 35 of the flexible substrate 15 so that electrical connection to a data acquisition device (not shown), and/or an amplifier (not shown), can be made. The contact 25 and area 40 are connected by a thin metal strip 45, as shown in FIG. 1A. The interconnecting metal strip is biocompatible according to one embodiment of the invention. The interconnecting metal strip is preferably highly conductive and malleable and further preferably resistant to oxidation. Accordingly to a preferred embodiment of the invention, the interconnecting metal strip preferably comprises an approximately 20 nm thick layer of titanium and an approximately 150 nm thick layer of gold that are preferably electron beam evaporated. The titanium enhances adhesion of the gold to the polyimide surface of the flexible substrate. It is also biocompatible. Gold is preferably utilized as the main interconnect metal because of its high electrical conductivity, biocompatibility, malleability and resistance to oxidation.

The entire flexible substrate 15 is preferably covered with an electrically insulating film 50 except at the contact surface of the electrodes and the region at the edge of the substrate where the connections to data acquisition devices are made. The film 50 is preferably a silicone film which is approved for long term implants. The only materials that contact the patient are the materials of the film 50 and the contacts 25, that is, preferably the silicone film and platinum.

The fabrication sequence for small electrodes (<approximately 100 µm diameter) may include photolithography for the interconnecting metal strip, deposition of, for example, titanium and gold by electron beam evaporation, patterning of the titanium and gold by lift-off, deposition of the insulating film, etching of the film and electroplating, for example, platinum to obtain the raised electrode. For large electrodes (>approximately 100 µm diameter), the fabrication may include photolithography for the interconnecting metal stip, deposition of, for example, titanium, gold and platinum by electron beam evaporation, patterning of the metals by lift-off, embossing the substrate to raise the electrodes, deposition of the insulating film and etching of the film.

In spite of the relatively thin and narrow metal features, the interconnecting strips are not damaged by normal handling. This durability is due to the fact that the gold to plastically deforms rather than cracks when the substrate is bent.

Figures 3A, 3B:
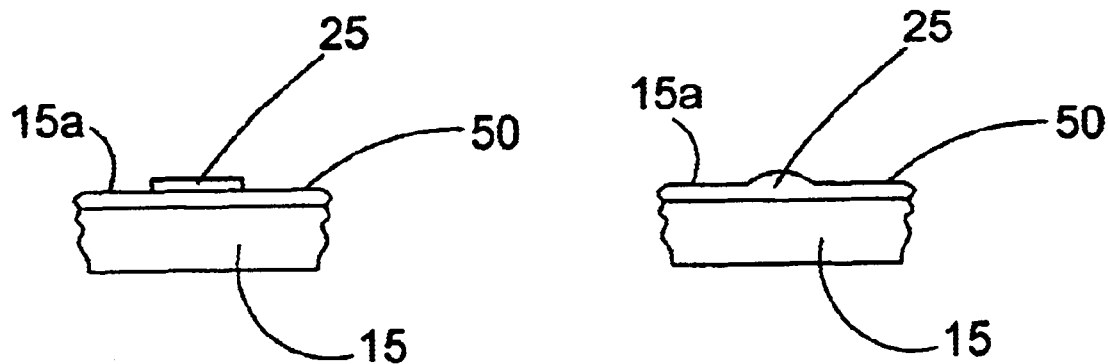
FIGS. 3A–3B show various embodiments of the shape of the electrode contact of an electrode array according to preferred embodiments of the invention.

The contact 25 is preferably deposited either by electron beam evaporation or by electroplating; however, other methods of fabrication may also be appropriate. For example, platinum may be evaporated for larger electrodes and electroplated for smaller electrodes. Preferably, the surfaces of the electrodes are built up above the surface 15a of the substrate 15 to improve electrical contact to the brain, as shown in FIGS. 3A–3B. The raised electrodes should preferably be flat, as shown in FIG. 3A, or rounded, as shown in FIG. 3B, rather than pointed, to limit the contact pressure when applied to the brain. However, other shapes may also be appropriate.

For example, for small electrodes (<approximately 100 µm diameter), the electrodes may be formed by electroplating platinum up to extend above the substrate surface, for example, up to approximately 10 µm to 50 µm above the surface, more preferably approximately 20 µm above the substrate surface. Because the electroplating is diffusion-limited, the electrode surface is higher near the periphery than at the center. For larger electrodes (>approximately 100 µm diameter), it is more difficult to obtain the desired surface profile. Thus, larger electrodes may be formed, for example, embossing the substrate. For example, using the second process, platinum may be added to the electrode surface by electron beam evaporation as part of the metallization step that creates the connecting metal strip.

Completed electrode arrays with an intercontact separation of approximately 120 µm and contact diameter of approximately 60 µm have been tested on cats. The signal was comparable to that from larger commercial electrodes.

The process described herein can be utilized to make neurological electrode arrays for use in humans and other mammals. The process can be scaled for smaller and more densely packed arrays and for a larger number of electrodes than provided by currently commercially available devices.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A biocompatible electrode array configured to conform to a brain of a mammal, comprising:
   a flexible substrate formed of polyimide; and
   a plurality of electroplated electrodes disposed on the flexible substrate, each of said electrodes having a diameter less than approximately 100 µm and extending approximately 10 µm to 50 µm above a surface of said flexible substrate to yield a desired surface profile for electrical contact to said brain.

2. The electrode array of claim 1, wherein the flexible substrate is formed of a polyimide film having a thickness of approximately 0.003".

3. The electrode array of claim 1, wherein each of the plurality of electrodes comprises a contact, wherein the contact is formed of platinum.

4. The electrode array of claim 3, wherein the contact is configured to have a rounded upper surface.

5. The electrode array of claim 3, wherein the contact is configured to have a flat upper surface.

6. The electrode array of claim 3, wherein each of the plurality of electrodes further comprises an area for making an electrical connection to an electrical device, and wherein the contacts and the areas of each of the plurality of electrodes are connected by a metal strip, the metal strip comprising a layer of titanium and a layer of gold.

7. The electrode array of claim 6, wherein the layer of titanium is approximately 20 nm in thickness and the layer of gold is approximately 150 nm in thickness.

8. The electrode array of claim 6, wherein the flexible substrate is covered in an electrically insulating film except at the portions of the flexible substrate where the contacts and the electrical connection areas of the electrodes are located.

9. The electrode array of claim 8, wherein the electrically insulating film is comprises a silicone film.

10. A biocompatible electrode array configured to conform to a brain of a mammal, comprising:
    a flexible substrate;
    a plurality of electroplated electrodes disposed on the flexible substrate, wherein each of the electrodes comprises a contact, wherein each of the contacts has a diameter less than approximately 100 µm, each of said electrodes having a diameter less than approximately 100 µm and extending approximately 10 µm to 50 µm above a surface of said flexible substrate to yield a desired surface profile for electrical contact to said brain.

11. The electrode array of claim 10, wherein the flexible substrate is formed of polyimide.

12. The electrode array of claim 11, wherein the flexible substrate is formed of a polyimide film having a thickness of approximately 0.003".

13. The electrode array of claim 10, wherein each of the plurality of electrodes comprises a contact, wherein the contact is formed of platinum.

14. The electrode array of claim 10, wherein the contact is configured to have a rounded upper surface.

15. The electrode array of claim 10, wherein the contact is configured to have a flat upper surface.

16. The electrode array of claim 10, wherein each of the plurality of electrodes further comprises an area for making an electrical connection to an electrical device, and wherein the contacts and the areas of each of the plurality of electrodes are connected by a metal strip, the metal strip comprising a layer of titanium and a layer of gold.

17. The electrode array of claim 16, wherein the layer of titanium is approximately 20 nm in thickness and the layer of gold is approximately 150 nm in thickness.

18. The electrode array of claim 16, wherein the flexible substrate is covered in an electrically insulating film except at the portions of the flexible substrate where the contacts and the electrical connection areas of the electrodes are located.

19. The electrode array of claim 18, wherein the electrically insulating film is formed of a silicone film.

20. A biocompatible electrode array configured to conform to brain of a mammal, comprising:

a flexible substrate having upper and lower surfaces;

a plurality of electroplated electrodes disposed on the flexible substrate, each of the plurality of electrodes having a contact, an area for making electrical connection to an electrical device, and a diameter less than approximately 100 $\mu$m and extending approximately 10 $\mu$m to 50 $\mu$m above a surface of said flexible substrate to yield a desired surface profile for electrical contact to said brain; and an electrically insulating film covering both the upper and lower surfaces of the substrate except at at least some portions of the substrate containing the contacts and the electrical connection areas of the plurality of electrodes.

21. The electrode array of claim 20, wherein the flexible substrate is formed of polyimide.

22. The electrode array of claim 21, wherein the flexible substrate is formed of a polyimide film having a thickness of no more than approximately 0.003".

23. The electrode array of claim 20, wherein the contact of each of the plurality of electrodes comprises platinum.

24. The electrode array of claim 23, wherein the contact of each of the plurality of electrodes is configured to have a rounded upper surface.

25. The electrode array of claim 23, wherein the contact of each of the plurality of electrodes is configured to have a flat upper surface.

26. The electrode array of claim 23, wherein the contacts and the areas of each of the plurality of electrodes are connected by a metal strip, the metal strip comprising a layer of titanium and a layer of gold.

27. The electrode array of claim 26, wherein the layer of titanium is approximately 20 nm in thickness and the layer of gold is approximately 150 nm in thickness.

28. The electrode array of claim 20, wherein the electrically insulating film is comprises a silicone film.

29. A biocompatible electrode array configured to conform to a brain of a mammal, comprising:

a thin flexible substrate capable of conforming to a brain of an animal; and a plurality of electroplated electrodes disposed on the thin flexible substrate, wherein the plurality of electrodes comprise a plurality of contacts configured to contact the brain, wherein the thin flexible substrate is capable of tolerating microfabrication, and wherein the flexible substrate is formed of a polyimide film having a thickness of approximately 0.003", and wherein each of said electrodes has a diameter less than approximately 100 $\mu$m and extending approximately 10 $\mu$m to 50 $\mu$m above a surface of said flexible substrate to yield a desired surface profile for electrical contact to said brain.

* * * * *